United States Patent
Barbera-Guillem

(10) Patent No.: US 6,309,701 B1
(45) Date of Patent: *Oct. 30, 2001

(54) FLUORESCENT NANOCRYSTAL-LABELED MICROSPHERES FOR FLUORESCENCE ANALYSES

(75) Inventor: Emilio Barbera-Guillem, Powell, OH (US)

(73) Assignee: Bio-Pixels Ltd., Westerville, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 09/577,761

(22) Filed: May 24, 2000

Related U.S. Application Data

(63) Continuation-in-part of application No. 09/372,729, filed on Aug. 11, 1999, now Pat. No. 6,114,038
(60) Provisional application No. 60/107,829, filed on Nov. 10, 1998.

(51) Int. Cl.$^7$ .............. A61K 49/00; B05D 7/00; B32B 9/00; B32B 9/04; H01L 29/04
(52) U.S. Cl. .............. 427/213.3; 427/214; 427/215; 427/220; 428/402.24; 428/404; 424/9.1; 424/9.32; 424/9.36; 424/9.42; 424/9.6; 257/65; 257/614; 257/642
(58) Field of Search .................. 427/213.3, 214, 427/215, 220; 428/402.24, 404; 424/9.1, 9.32, 9.36, 9.42, 9.6; 257/65, 614, 642

(56) References Cited

U.S. PATENT DOCUMENTS

| 5,194,300 | 3/1993 | Cheung . |
| 5,747,349 | 5/1998 | van den Engh et al. . |
| 5,990,479 | 11/1999 | Weiss et al. . |
| 6,114,038 | * 9/2000 | Castro et al. .......... 428/402.24 |
| 6,207,392 | 3/2001 | Weiss et al. . |

* cited by examiner

Primary Examiner—Nathan M. Nutter
(74) Attorney, Agent, or Firm—M. Bud Nelson

(57) ABSTRACT

Provided are a fluorescent microsphere comprised of a plurality of fluorescent nanocrystals operably bound to a polymeric microsphere, and a method of producing the fluorescent microspheres which comprises contacting the polymeric microsphere with a plurality of fluorescent nanocrystals under suitable conditions in which the fluorescent naocrystals become operably bound to the polymeric microsphere. Also provided is a method of using the fluorescent microspheres capable of determining the presence or absence of a predetermined number of analytes in a sample by contacting the sample with the fluorescent microspheres, and detecting the fluorescence signal pattern of excited fluorescent microspheres bound to one or more analytes of the predetermined number of analytes, if present in the sample.

39 Claims, 1 Drawing Sheet

US 6,309,701 B1

FLUORESCENT NANOCRYSTAL-LABELED MICROSPHERES FOR FLUORESCENCE ANALYSES

This is a continuation-in-part application based on co-pending U.S. Ser. No. 09/372,729 filed on Aug. 11, 1999 which is now U.S. Pat. No. 6,114,038 and non provisional application based on U.S. Ser. No. 60/107,829 filed on Nov. 20, 1998, the disclosures of which are herein incorporated by reference.

FIELD OF THE INVENTION

This invention relates to polymer-based microspheres, wherein the microspheres are labeled with one or more types of fluorescent nanocrystals. The resulting fluorescent microspheres are useful as distinct tagging agents or as encoders in methods utilizing fluorescence-based detection such as microarrays, high-throughput screening, immunoassays, and flow cytometry.

BACKGROUND OF THE INVENTION

Fluorescent polymeric microspheres have been described as comprising either microspheres which are surface-labeled (including surface-coated) with fluorescent dyes, or microspheres having structurally incorporated within their volume (e.g., embedded or polymerized therein) a fluorescent dye. Commonly used fluorescence-based analyses that utilize fluorescent microspheres generally apply the microspheres for a purpose selected from the group consisting of: as a detection reagent with an affinity ligand bound thereto in assaying for the presence of a molecule for which the affinity ligand has binding specificity, as a calibrating agent for calibrating fluorescence-based detection systems, as a tracer (e.g., to trace the flow of a fluid containing the microspheres), and a combination thereof.

Typically, conventional fluorescent dyes (e.g., fluorescein, rhodamine, phycoerythrin, and the like) are used for labeling microspheres. These conventional fluorescent dyes typically have an excitation spectrum that may be quite narrow; hence, it is often difficult to find a wavelength spectrum of light suitable for simultaneously exciting several different fluorescent labels (e.g., differing in color of fluorescence emission). However, even when a single light source is used to provide a excitation wavelength spectrum (in view of the spectral line width), often there is insufficient spectral spacing between the emission optima of different species (e.g., differing in color) of fluorescent dyes to permit individual and quantitative detection without substantial spectral overlap. Additionally, conventional fluorescent dyes are susceptible to photobleaching which limits the time in which a fluorescent signal can be detected, and limits time-resolved fluorescence (fluorescent signal integration over time). Additional limitations of fluorescent dyes include fluorescence quenching, and shifts in fluorescence emission spectra, depending on the environment in which dyes are excited.

Fluorescent nanocrystals comprising either semiconductor nanocrystals or doped metal oxide nanocrystals have been reported to resist photobleaching, share an excitation wavelength spectrum, and are capable of emitting fluorescence of high quantum yield and with discrete peak emission spectra. However, these nanocrystals lack sufficient solubility in aqueous-based environments required for labeling microspheres; i.e., in aqueous-based environments, the nanocrystals interact together in forming aggregates, which leads to irreversible flocculation of the nanocrystals.

Thus, there remains a need for fluorescent microspheres that: (a) may be used in either single color or multicolor analysis; (b) are comprised of fluorescent nanocrystals which are sufficiently soluble in aqueous-based solutions to permit an effective concentration of the fluorescent nanocrystals to be operably bound to polymeric microspheres in forming fluorescent microspheres; (c) which may be excited with a single wavelength spectrum of light resulting in detectable fluorescence of high quantum yield and with discrete peak emission spectra; (d) that are not susceptible to photobleaching and (e) which may further comprise one or more molecules of affinity ligand for use in fluorescence-based detection systems.

SUMMARY OF THE INVENTION

Provided is a fluorescent microsphere comprised of a polymeric microsphere that is operably bound to a plurality of at least one type of fluorescent nanocrystals, such that following excitation of the fluorescent microsphere with an appropriate excitation wavelength spectrum, the fluorescent microsphere will emit fluorescence of high quantum yield and with discrete peak emission. Fluorescent microspheres may differ in size and composition, and can be varied in the intensity of fluorescence emission and the one or more colors of fluorescence emission by changing the amount and type of fluorescent nanocrystals, respectively, in the method of preparing the microspheres. Thus, the fluorescent properties of the fluorescent microspheres, such as intensity and color, is sensitive to the corresponding fluorescent nanocrystals used to produce the fluorescent microspheres. A resultant advantage of the fluorescent microspheres of the present invention is that they may be produced to have a far greater degree of fluorescence (intensity) than previously known fluorescent microspheres. Additionally, the fluorescent microspheres may be used for measuring a plurality of analytes in a single sample. For example, a first population of fluorescent microspheres may be (a) labeled with a plurality of one type of fluorescent nanocrystals which will emit a red fluorescent signal upon excitation, and (b) tagged with affinity ligand having binding specificity for a first analyte. A second population of fluorescent microspheres may be (a) labeled with a plurality of one type of fluorescent nanocrystals which will emit a yellow fluorescent signal upon excitation, and (b) tagged with affinity ligand having binding specificity for a second analyte. Thus, because the first and second populations of fluorescent microspheres can be excited with a single wavelength spectrum of light resulting in detectable fluorescence of high quantum yield and with discrete peak emission spectra, and because the first and second populations of fluorescent microspheres can bind their respective analyte (via their affinity ligand), the two populations of fluorescent microspheres can be mixed within one sample in simultaneously measuring for the presence of the first and second analytes.

Advantages of the fluorescent microspheres over individual nanocrystals which have been functionalized to include an affinity ligand, include the following. First, a single nanocrystal may only be functionalized with a limited number of affinity ligands. In contrast, a fluorescent microsphere according to the present invention can be labeled with a far greater number of fluorescent nanocrystals in enabling a fluorescent signal much greater in intensity than a single fluorescent nanocrystal can emit. Such an advantage is particularly useful in measuring an analyte which is present in minute quantities (and hence, can be bound by only a limited number of affinity ligand). Additionally, more than one type of fluorescent nanocrystal may be used to label the fluorescent microspheres. Hence, the fluorescent microspheres may comprise a plurality of types of fluorescent nanocrystals in encoding the fluorescent microspheres with a specific, identifiable code (based on the emission spectra which can comprise both color and intensity) which can be used to distinguish this population of microspheres from a population of fluorescent microspheres which encoded with a different fluorescence pattern. Such encoded fluorescent microspheres are particularly suited for multidimensional microarray formats. Further, in a method of producing the fluorescent microspheres according to the present invention, by controlling the proportion of starting materials (e.g., number of polymeric microspheres, and the number and composition of fluorescent nanocrystals), precise control may be achieved with respect to the basic fluorescent properties of the resultant fluorescent microspheres.

The above and other objects, features, and advantages of the present invention will be apparent in the following Detailed Description of the Invention when read in conjunction with the accompanying drawings.

DETAILED DESCRIPTION OF THE INVENTION

Definitions

Figure 1:
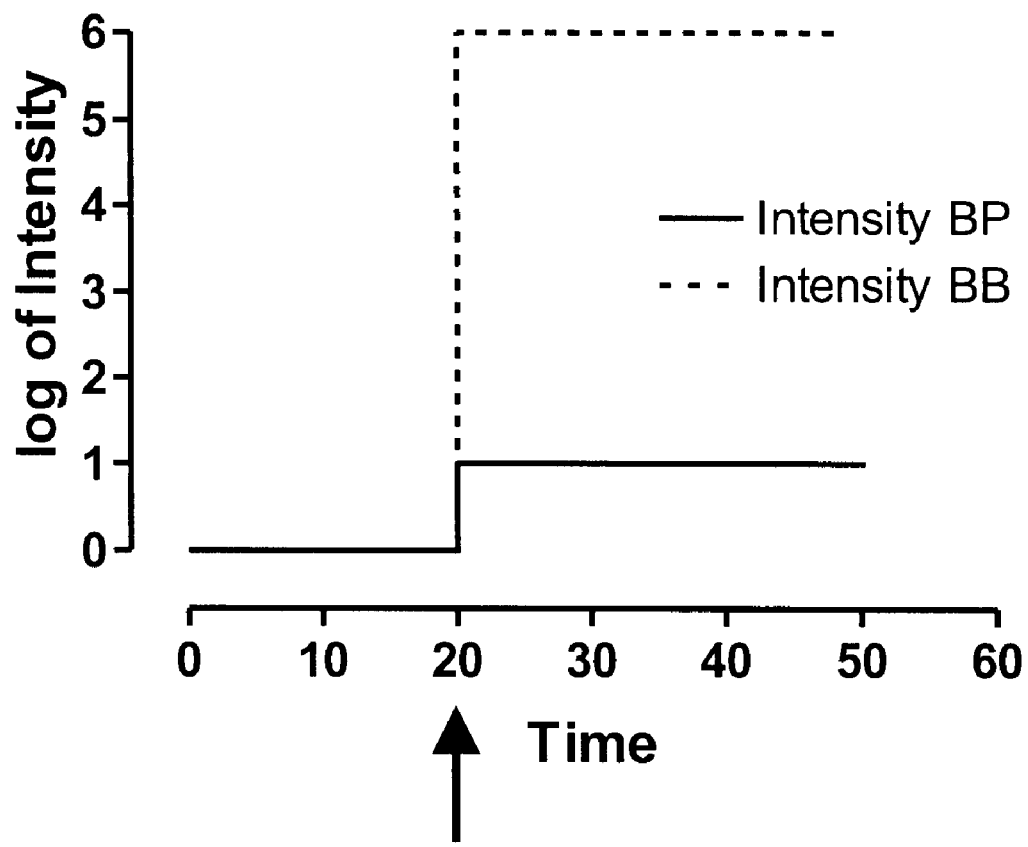
FIG. 1 is a graph illustrating the relative intensity of an exemplary fluorescent microsphere according to the present invention, as compared to that of a fluorescent nanocrystal.

By the term "analyte" is meant, for the purposes of the specification and claims to refer to a molecule of an organic or inorganic nature, the presence and/or quantity of which is being tested for; and which contains a molecular component (domain or sequence or epitope or portion or chemical group or determinant) for which the affinity ligand has binding specificity. The molecule may include, but is not limited to, a nucleic acid molecule, protein, glyco-protein, eukaryotic or prokaryotic cell, lipoprotein, peptide, carbohydrate, lipid, phospholipid, aminoglycans, chemical messenger, biological receptor, structural component, metabolic product, enzyme, antigen, drug, therapeutic, toxin, inorganic chemical, organic chemical, and the like.

By the term "affinity ligand" is meant, for purposes of the specification and claims, to mean a molecule which has binding specificity and avidity for a molecular component of, or associated with, an analyte. In general, affinity ligands are known to those skilled in the art to include, but are not limited to, lectins or fragments (or derivatives) thereof which retain binding function; monoclonal antibodies ("mAb", including chimeric or genetically modified monoclonal antibodies (e.g., "humanized")); peptides; aptamers; nucleic acid molecules (including, but not limited to, single stranded RNA or single-stranded DNA, or single-stranded nucleic acid hybrids); avidin, or streptavidin, or avidin derivatives; and the like. The invention may be practiced using a preferred affinity ligand (e.g., a mAb) to the exclusion of affinity ligands other than the preferred affinity ligand. The term "monoclonal antibody" is also used herein, for purposes of the specification and claims, to include immunoreactive fragments or derivatives derived from a mAb molecule, which fragments or derivatives retain all or a portion of the binding function of the whole mAb molecule. Such immunoreactive fragments or derivatives are known to those skilled in the art to include F(ab')$_2$, Fab', Fab, Fv, scFV, Fd' and Fd fragments. Methods for producing the various fragments or derivatives from mAbs are well known in the art (see, e.g., Plückthum, 1992, Immunol. Rev. 130:152–188). For example, F(ab')$_2$ can be produced by pepsin digestion of the monoclonal antibody, and Fab' may be produced by reducing the disulfide bridges of F(ab')$_2$ fragments. Fab fragments can be produced by papain digestion of the monoclonal antibody, whereas Fv can be prepared according to methods described in U.S. Pat. No. 4,642,334. Single chain antibodies can be produced as described in U.S. Pat. No. 4,946,778. Aptamers can be made using methods described in U.S. Pat. No. 5,789,157 (herein incorporated by reference). Lectins, and fragments thereof, are commercially available.

By the term "fluorescent microsphere" is meant, for purposes of the specification and claims to refer to a plurality of fluorescent nanocrystals operably bound to a polymeric microsphere.

By the term "polymeric microsphere" is meant, for purposes of the specification and claims to refer to a bead which is substantially spherical in shape, and is comprised of a polymeric material which may include, but is not limited to, latex, acrylic, glass/polymer composites (see, e.g., U.S. Pat. No. 5,507,990), a thermoplastic (e.g., one or more of polystyrenes, polyvinyl chloride, polyacrylate, nylon, substituted styrenes, polyamides, polycarbonate, polymethylacrylic acids, polyaldehydes, and the like), a magnetic material in combination with a polymeric material, and a combination thereof. In one embodiment, the polymeric material may further comprise carbon black in a % weight in a range of from about 0.5 to about 5 with respect to the polymeric material, which may minimize (reduce or quench) intrinsic fluorescence of the polymeric material, if any. For example, the carbon black may be mixed into a solution of a thermoplastic, and then the mixture is plasticized into a solid composite. In a preferred embodiment, the polymeric microspheres may further comprise one or more molecules of affinity ligand operably bound thereto. Methods for operably binding affinity ligand to the surface of polymeric microspheres are well known in the art. Depending on the composition of the polymeric microspheres, typically the microspheres will comprise one or more types of reactive functionalities which react with reactive functionalities of an affinity ligand resulting in affinity ligand being operably bound to the polymeric microspheres. In a preferred embodiment, the one or more types of reactive functionalities present on the surface of the polymeric microsphere comprises a plurality of carboxyl-reactive groups, a plurality of amine-reactive groups, or a combination thereof. In a preferred embodiment, the average diameter of the polymeric sphere is in a range of from about 0.05 micron ($\mu$m) to about 500 $\mu$m; and most preferably, in a range of from about 0.1 $\mu$m to about 10 $\mu$m. As will be appreciated by those skilled in the art, the composition, shape, size, and density of the polymeric microsphere may vary depending on the factors such as the assay system in which it is used, as well as the nature of an analyte to be detected. A preferred polymeric microsphere may be used to the exclusion of a polymeric microsphere other than the preferred polymeric microsphere.

By the term "fluorescent nanocrystals" is meant, for purposes of the specification and claims to refer to nanocrystals comprising semiconductor nanocrystals or doped metal oxide nanocrystals, wherein the nanocrystals are operably bound to, and functionalized by the addition of, a plurality of molecules which provide the functionalized fluorescent nanocrystals with reactive functionalities to enable the fluorescent nanocrystals to become operably bound to the polymeric microspheres in forming the fluorescent microspheres according to the present invention. In a preferred plurality of molecules is selected from the group consisting of carboxylic acid, diaminocarboxylic acid, a monoaminocarboxylic acid, and a combination thereof. A preferred type of molecules may be used to the exclusion of molecules other than the preferred type of molecules. In a preferred embodiment, the functionalized nanocrystals are sufficiently soluble in an aqueous-based environment to permit the fluorescent nanocrystals to be operably bound to the polymeric microspheres in forming fluorescent microspheres in an aqueous-based environment.

By the term "semiconductor nanocrystals" is meant, for purposes of the specification and claims to refer to quantum dots (crystalline semiconductors) comprised of a core comprised of at least one of a Group II–VI semiconductor material (of which ZnS, and CdSe are illustrative examples), or a Group III–V semiconductor material (of which GaAs is an illustrative example), a Group IV semiconductor material, or a combination thereof. In a preferred embodiment, the core of the quantum dots may be passivated with an semiconductor overlayering ("shell") uniformly deposited thereon. For example, a Group II–VI semiconductor core may be passivated with a Group II–VI semiconductor shell (e.g., a ZnS or CdSe core may be passivated with a shell comprised of YZ wherein Y is Cd or Zn, and Z is S, or Se). As known to those skilled in the art, the size of the semiconductor core correlates with the spectral range of emission. Table 1 is an illustrative example for CdSe.

TABLE 1

| Color | Size Range (nm) | Peak Emission Range |
|---|---|---|
| blue | 2.5 to 2.68 | 476 to 486 |
| green | 2.8 to 3.4 | 500 to 530 |
| yellow | 3.58 to 4.26 | 536 to 564 |
| orange | 4.9 to 6.1 | 590 to 620 |
| red | 8.6 to 10.2 | 644 to 654 |

In a preferred embodiment, the semiconductor nanocrystals are produced using a continuous flow process and system disclosed in copending U.S. application Ser. No. 09/468,418 (the disclosure of which is herein incorporated by reference), and have a particle size that varies by less than +/−4% in the average particle size. In a preferred embodiment, the semiconductor nanocrystals comprise a monodisperse population having an average particle size (as measure by diameter) in the range of approximately 1 nanometer (nm) to approximately 20 nm.

By the term "doped metal oxide nanocrystals" is meant, for purposes of the specification and claims to refer to nanocrystals comprised of: a metal oxide, and a dopant comprised of one or more rare earth elements. For example, suitable metal oxides include, but are not limited to, yttrium oxide ($Y_2O_3$), zirconium oxide ($ZrO_2$), zinc oxide (ZnO), copper oxide (CuO or $Cu_2O$), gadolinium oxide ($Gd_2O_3$), praseodymium oxide ($Pr_2O_3$), lanthanum oxide ($La_2O_3$), and alloys thereof. The rare earth element comprises an element selected from the Lanthanide series and includes, but is not limited to, europium (Eu), cerium (Ce), neodymium (Nd), samarium (Sm), terbium (Tb), gadolinium (Gd), holmium (Ho), thulium (Tm), an oxide thereof, and a combination thereof. As known to those skilled in the art, depending on the dopant, an energized doped metal oxide nanocrystal is capable of emitting light of a particular color. Thus, the nature of the rare earth or rare earths are selected in consequence to the color sought to be imparted (emitted) by a doped metal oxide nanocrystal used to label a microsphere according to the present invention. A given rare earth or rare earth combination has a given color, thereby permitting the provision of doped metal oxide nanocrystals, each of which may emit (with a narrow emission peak) a color over an entire range of colors by adjusting the nature of the dopant, the concentration of the dopant, or a combination thereof. For example, the emission color and brightness (e.g., intensity) of a doped metal oxide nanocrystal comprising $Y_2O_3$:Eu may depend on the concentration of Eu; e.g., emission color may shift from yellow to red with increasing Eu concentration. For purposes of illustration only, representative colors which may be provided are listed in Table 2.

TABLE 2

| Fluorescent Color | Dopant |
|---|---|
| blue | thulium |
| blue | cerium |
| yellow-green | terbium |
| green | holmium |
| green | erbium |
| red | europium |
| reddish orange | samarium |
| orange | neodymium |
| yellow | dysprosium |
| white | praseodymium |
| orange-yellow | europium + terbium |
| orange-red | europium + samarium |

Methods for making doped metal oxide nanocrystals are known to include, but are not limited to, a sol-gel process (see, e.g., U.S.. Pat. No. 5,637,258), and an organometallic reaction. As will be apparent to one skilled in the art, the dopant (e.g., one or more rare earth elements) are incorporated into the doped metal oxide nanocrystal in a sufficient amount to permit the doped metal oxide nanocrystal to be put to practical use in fluorescence detection as described herein in more detail. An insufficient amount comprises either too little dopant which would fail to emit sufficient detectable fluorescence, or too much dopant which would cause reduced fluorescence due to concentration quenching. In a preferred embodiment, the amount of dopant in a doped metal oxide nanocrystal is a molar amount in the doped metal oxide nanocrystal selected in the range of from about 0.1% to about 25%. Doped metal oxide nanocrystals may can be excited with a single excitation light source resulting in a detectable fluorescence emission of high quantum yield (e.g., a single quantum dot having at a fluorescence intensity that may be a log or more greater than that a molecule of a conventional fluorescent dye) and with a discrete fluorescence peak. Typically, they have a substantially uniform size of less than 200 Angstroms, and preferably have a substantially uniform size in the range of sizes of from about 1 nm to about 5 nm, or less than 1 nm. In a preferred embodiment, the doped metal oxide nanocrystals are comprised of metal oxides doped with one or more rare earth elements, wherein the dopant comprising the rare earth element is capable of being excited (e.g., with ultraviolet light) to produce a narrow spectrum of fluorescence emission. In another preferred embodiment, the doped metal oxide has both fluorescent properties (when excited with an excitation light source) and magnetic properties; thus, a polymeric microsphere (which is substantially nonmagnetic) operably bound to a plurality of fluorescent nanocrystals (comprising doped metal oxide nanocrystals which are magnetic material) may form fluorescent microspheres according to the present invention which are magnetic.

By the term "operably bound" is meant, for purposes of the specification and claims to refer to fusion or bond or an association of sufficient stability to withstand conditions encountered in a method of detection, between a combination of different molecules such as, but not limited to, between the functionalized nanocrystal and the polymeric microsphere, and between a fluorescent nanocrystal and the molecules by which they are functionalized (e.g., carboxylic acid, diaminocarboxylic acid, or a monoaminocarboxylic acid), and a combination thereof. As known to those skilled in the art, the bond may comprise one or more of covalent, ionic, hydrogen, van der Waals, and the like. As known to those skilled in the art, and as will be more apparent by the following embodiments, there are several methods and compositions in which two or more molecules may be operably bound utilizing reactive functionalities. Reactive functionalities include, but are not limited to, free chemical groups (e.g., thiol, or carboxyl, hydroxyl, amino, amine, sulfo, etc.), and reactive chemical groups (reactive with free chemical groups).

The term "suitable conditions" is used herein, for purposes of the specification and claims, and with reference to a process of reacting two components (e.g., polymeric microsphere and fluorescent nanocrystals; fluorescent microsphere comprising affinity ligand and an analyte for which the affinity ligand has binding specificity), to mean those conditions under which the components may become operably bound to each other. As known to those skilled in the art, such conditions may include one or more of: a pH range of from about 3 to about 9, ionic strengths such as that ranging from distilled water to about 1 molar sodium chloride, and a temperature in the range of from about 4° C. to about 45° C.; and may further include a time sufficient for binding to occur (e.g., in a range of from about 10 minutes to about 2 hours).

By the term "diaminocarboxylic acid" is meant, for purposes of the specification and claims to refer to an amino acid that has two free amine groups. The amino acid may be a naturally occurring amino acid, a synthetic amino acid, a modified amino acid, an amino acid derivative, and an amino acid precursor (e.g., citrulline and ornithine are intermediates in the synthesis of arginine). In a preferred embodiment, the diaminocarboxylic acid contains neutral (uncharged) polar functional groups which can hydrogen bond with water, thereby making the diaminocarboxylic acid (and the quantum dot to which it is made a part of) relatively more soluble in aqueous solutions containing water than those with nonpolar functional groups. Exemplary diaminocarboxylic acids include, but are not limited to, lysine, asparagine, glutamine, arginine, citrulline, ornithine, 5-hydroxylysine, djenkolic acid, β-cyanoalanine, and synthetic diaminocarboxylic acids such as 3,4-diaminobenzoic acid, 2,3-diaminopropionic acid, 2,4-diaminobutyric acid, 2,5-diaminopentanoic acid, and 2,6-diaminopimelic acid.

By the term "amino acid" is meant, for purposes of the specification and claims to refer to a molecule that has at least one free amine group and at least one free carboxyl group. The amino acid may have more than one free amine group, or more than one free carboxyl group, or may further comprise one or more free chemical reactive groups other than an amine or a carboxyl group (e.g., a hydroxyl, a sulfhydryl, etc.). The amino acid may be a naturally occurring amino acid, a synthetic amino acid, a modified amino acid, an amino acid derivative, and an amino acid precursor. The amino acid may further be selected from the group consisting of a monoaminocarboxylic acid, and a diaminocarboxylic acid. In a preferred embodiment, the monoaminocarboxylic acid contains one or more neutral (uncharged) polar functional groups which can hydrogen bond with water, thereby making the monoaminocarboxylic acid (and the quantum dot to which it is made a part of) relatively more soluble in aqueous solutions containing water than those with non-polar functional groups. Exemplary monoaminocarboxylic acids include, but are not limited to, glycine, serine, threonine, cysteine, βalanine, homoserine, γ-aminobutyric acid, and homocysteine.

By the term "carboxylic acid" is meant, for purposes of the specification and claims to refer to a compound having the formula $HS(CH_2)_nX$, wherein X is a carboxylate (carboxylic moiety). "n" is a number in the range of from 1 to about 20, and preferably greater than 4. In a preferred embodiment, the thiol group of the carboxylic acid can be used as a reactive functionality for the carboxylic acid to become operably bound to the nanocrystal, depending on the composition of the nanocrystal (e.g., to Cd, Zn and the like). Additionally, the carboxylic moiety of the carboxylic acid imparts water solubility to the nanocrystals. Exemplary carboxylic acids may include, but are not limited to, mercaptocarboxylic acid, or mercaptofunctionalized amines (e.g., aminoethanethiol-HCl, or 1-amino-2-methyl-2-propanethiol-HCl).

The following examples are illustrative of the methods and fluorescent microspheres of the present invention.

EXAMPLE 1

As disclosed in detail in U.S. application Ser. No. 09/372,729 (the disclosure of which is herein incorporated by reference), fluorescent nanocrystals comprise nanocrystals which have been functionalized by the addition of a plurality of molecules; and preferably, the molecules are selected from an amino acid, a carboxylic acid, and a combination thereof. For example, the nanocrystals may comprise semiconductor nanocrystals that have a core selected from the group consisting of CdSe, CdS, and CdTe (collectively referred to as "CdX"), and may further comprise a passivating shell comprised of YZ wherein Y is Cd or Zn, and Z is S, or Se. Typically, CdX core/YZ shell quantum dots are overcoated with trialkylphosphine oxide, with the alkyl groups most commonly used being butyl and octyl. In one preferred embodiment, the CdX cor/YZ shell quantum dots are treated with a large excess of mercaptocarboxylic acid in exchanging the trialkylphosphine oxide coat with a coat comprising a plurality of carboxylic acid molecules. For example, (CdSe)ZnS nanocrystals were prepared in a pyridine solution. The pyridine overcoating of the (CdX) core/YZ shell nanocrystals were exchanged with a carboxylic acid comprising mercaptocarboxylic acid. Exchange of the coating group is accomplished by treating the water-insoluble, pyridine-capped quantum dots with a large excess of neat mercaptocarboxylic acid. To accomplish this, the pyridine-capped (CdSe)ZnS quantum dots were precipitated with hexanes, and then isolated by centrifugation. The residue was dissolved in neat mercaptoacetic acid, with a few drops of pyridine added, if necessary, to form a transparent solution. Chloroform was added to precipitate the nanocrystals and wash away excess thiol. The nanocrystals were isolated by centrifugation, washed once more with chloroform, and then washed with hexanes. The residue was briefly dried with a stream of argon. The resultant nanocrystals, coated with molecules of carboxylic acid, were then soluble in water or other aqueous solutions. The nanocrystals, in an aqueous solution, were centrifuged once more, filtered through a 0.2 μm filter, degassed with argon, and stored in an amber vial. The nanocrystals may then be further functionalized by an amino acid comprising a diaminocarboxylic acid. The diaminocarboxylic acid molecules were operably bound to the carboxylic acid molecules of the nanocrystals by using commercially available crosslinking agents and methods known to those skilled in the art. For example, the carboxylic acid-coated nanocrystals were dissolved in an aqueous buffer system (pH of about 7). To the nanocrystals was added EDC (1-ethyl-3-[3-dimethylaminopropyl] carbodiimide) and sulfoNHS (sulfo-N-hydroxysuccinimide) in 500–1000 times excess. The resulting solution was stirred at room temperature for 30 minutes. Mercaptoethanol was added to neutralize unreacted EDC at 20 mM concentration and stirred for 15 minutes. The entire solution was then added dropwise, with stirring, to a solution of a diaminocarboxylic acid comprising lysine (large excess) in the same buffer; and the mixture was stirred for 2 hours at room temperature. Ethanolamine (30 mM) was added to quench the reaction; and the mixture was stirred for 30 minutes at room temperature or left overnight at 4° C. The solution was centrifuged to remove any precipitated solids, and then ultrafiltered through a 30 kD MW centrifugal filter. The resultant concentrated, fluorescent nanocrystals can be solubilized in an aqueous solution of choice. Once solubilized, the resulting solution can be stored in an amber vial under an inert gas to prevent flocculation. The fluorescent nanocrystals may be operably bound to a successive layer of amino acid molecules by, for example, repeating the procedure and reaction using EDC and sulfoNHS with the amino acid molecules comprising the successive layer.

Similarly, a nanocrystal comprising a doped metal oxide nanocrystal may be operably bound to a plurality of molecules (e.g., a carboxylic acid, and amino acid, or a combination thereof) using methods known in the art. For example, the plurality of molecules having reactive functionalities comprising free carboxyl groups can be chemisorbed, adsorbed or otherwise permanently added to the metal oxide portion of the nanocrystal. For example, the metal oxide nanocrystals are suspended in an aqueous solution of an amino acid comprising homocysteine having a pH of about 3.5 for about an hour. The reaction is then stopped by adjusting the pH to neutral, and dialyzing out the aqueous solution.

As an alternative, fluorescent nanocrystals functionalized with a plurality of homocysteine molecules were prepared as follows. Nanocrystals (e.g., (CdSe)ZnS) coated with an organic layer (e.g., mercaptoacetic acid) were treated with a molar excess of homocysteine in replacing the organic layer with a coating comprising a plurality of homocysteine molecules. The approximate number of surface Zn sites on the specific size of nanocrystals utilized was calculated. At least a 5 times molar excess of homocysteine (as compared to the number of surface Zn sites) was added to the nanocrystals, as per the following formula. Grams homocysteine=5(number of Zn surface sites)(volume of solution containing the nanocrystals)(concentration of nanocrystals in solution)(135.2). The mixture was stirred to dissolve the homocysteine, and then stored at 4° C. for 24 hours. The resultant solution was then centrifuged to remove any precipitate, and the supernatant was transferred to a centrifugal filter for the appropriate volume of supernatant (preferably, with a molecular weight cutoff of about 10 kD or below to retain the fluorescent nanocrystals coated with homocysteine). After centrifugation, and when the desired minimum volume is reached, the fluorescent nanocrystals were then rediluted in the appropriate aqueous solution (e.g., HEPES buffer) to a volume in which the original mass of homocysteine had been dissolved. The steps of filtering and redilution of the fluorescent nanocrystals in solution may be repeated to improve purity. The resultant fluorescent nanocrystals comprising homocysteine-coated nanocrystals may then be degassed by bubbling with an inert gas, and then stored at 4° C. in an amber bottle.

EXAMPLE 2

This example illustrates one embodiment of fluorescent microspheres, and a method of making the fluorescent microspheres, according to the present invention; wherein polymeric microspheres are contacted with fluorescent nanocrystals under suitable conditions for forming fluorescent microspheres. In a preferred embodiment, each polymeric microsphere comprises multiple molecules of reactive functionality comprising a free chemical group, and the fluorescent nanocrystals comprise multiple molecules of reactive functionality comprising reactive chemical groups which are capable of becoming operably bound to the reactive functionality of the polymeric microsphere under suitable conditions so that a plurality of fluorescent nanocrystals become operably bound to a polymeric microsphere in forming a fluorescent microsphere. For example, the polymeric microspheres comprise a reactive functionality comprising an amino group, and the fluorescent nanocrystals comprise a reactive functionality comprising an amino-reactive group (e.g., carboxyl or amine). In another illustrative example, the polymeric microspheres comprise a reactive functionality comprising a thiol group and the fluorescent nanocrystals comprise a reactive functionality comprising a thiolreactive group (e.g., amine group).

The polymeric microsphere used in this illustration comprised amine-activated polystyrene-based beads of a size of about 8.8 μm. More particularly, their composition comprised 25% styrene, 55% divinylbenzene, 20% glycidylmethacrylate, which was activated with ethylenediamine. Approximately $2.7 \times 10^6$ polymeric microspheres (in a volume of 100 μl aqueous solution) was mixed with 10 μl of a 10 μM fluorescent nanocrystal solution, and the mixture was gently agitated at room temperature for 20 minutes. The resultant fluorescent microspheres formed were then collected by centrifugation (e.g., 2 minutes at 2000×g), washed with an aqueous solution, and then collected by centrifugation again. To confirm the formation of fluorescent microspheres, the resultant microspheres were suspended in a nonaqueous medium (e.g., dimethylsulfoxide, or mineral oil, or heptane) and placed onto a slide for viewing under a fluorescence microscope. Alternatively, the solution containing the resultant microspheres was dried onto a slide for viewing under a fluorescence microscope. The results in Table 3 are illustrative of the fluorescence emitted by fluorescent microspheres according to the present invention. Type 1 fluorescent microspheres comprise fluorescent nanocrystals (homocysteine-coated (CdSe)ZnS) operably bound to amine-activated polymeric microspheres; type 2 fluorescent microspheres comprise fluorescent nanocrystals (homocysteine-coated (CdSe)ZnS; different in size than type 1) operably bound to amine-activated polymeric microspheres; type 3 fluorescent microspheres comprise fluorescent nanocrystals (mercaptocarboxylic acid-coated (CdSe) ZnS) operably bound to amine-activated polymeric microspheres; type 4 fluorescent microspheres comprise fluorescent nanocrystals ((CdSe)ZnS nanocrystals comprising a first coat comprising mercaptocarboxylic acid, and a second coat comprising diaminocarboxylic acid) operably bound to amine-activated polymeric microspheres; and a control comprising polymeric microspheres alone. In the fluorescence analyses, the excitation spectrum was from about 360 to about 380 nm. The resultant respective emission, as described by the color observed using the fluorescence microscope and the approximate peak emission wavelength, is listed for each of the type of microsphere.

TABLE 3

| Microsphere type | Fluorescence emission |
| --- | --- |
| type 1 | red (605 nm) |
| type 2 | green (545 nm) |
| type 3 | red (614 nm) |
| type 4 | yellow (573 nm) |
| control | — |

To further illustrate the attendant advantages of the fluorescent microspheres according to the present invention, FIG. 1 illustrates the relative intensity over time after excitation (arrow) of an exemplary fluorescent microsphere as compared to that of a comparative fluorescent nanocrystal used in producing a fluorescent microsphere.

EXAMPLE 3

This example illustrates another embodiment of fluorescent microspheres, and a method of making the fluorescent microspheres, according to the present invention; wherein polymeric microspheres are contacted with fluorescent nanocrystals under suitable conditions for forming fluorescent microspheres, and wherein the fluorescent microspheres further comprise a plurality of molecules of affinity ligand which are contacted with the fluorescent microspheres under suitable conditions for the affinity ligand to be operably bound to the fluorescent microspheres. In one preferred embodiment of the present invention, the polymeric microspheres have affinity ligand operably bound thereto before fluorescent nanocrystals are operably bound to the polymeric microspheres in producing fluorescent microspheres according to the present invention. In another preferred embodiment, fluorescent microspheres are produced first (e.g., by operably binding the fluorescent nanocrystals to the polymeric microspheres), and then the affinity ligand is operably bound to the fluorescent microspheres. In illustrating this latter preferred embodiment, fluorescent microspheres were made according to the methods described in Example 2 herein. To approximately $1.4 \times 10^7$ fluorescent microspheres (in a volume of 500 μl aqueous solution) was added 2 mg of EDC (in 100 μl aqueous solution) and 5 mg sulfo-NHS (in 100 μl aqueous solution), and the mixture was mixed for 10 minutes. Mercaptoethanol (1 μl) was added to the mixture with stirring for 5 minutes. Affinity ligand (in this illustrative embodiment, neutravidin; 10 μg) was added to the mixture with stirring for 1 hour. TRIS (30 mM) was then added to the mixture with stirring for 30 minutes. The resultant fluorescent microspheres were then pelleted by centrifugation, were washed several times in aqueous solution to wash away free neutravidin, and then resuspended in an aqueous solution.

The following example illustrates (a) a test that neutravidin was operably bound to the fluorescent microspheres; and (b) a method of using the fluorescent microspheres to detect an analyte in a sample. Approximately $1.4 \times 10^6$ fluorescent microspheres in 10 μl of aqueous solution was mixed and incubated with approximately $3 \times 10^5$ biotinylated polystyrene beads (6.7 μm in diameter) for 30 minutes at room temperature. The mixture comprising fluorescent microspheres and polystyrene beads was washed with aqueous solution and vigorously mixed to break up any clumping do to non-specific aggregation. The microspheres and beads were centrifuged, resuspended in DMSO, mixed again, and then mounted on a microscope slide with a coverslip. The slide was then examined under bright-field and fluorescence microscopy. The analysis showed that nearly all biotinylated polystyrene beads were bound to fluorescent microspheres. The observed binding included large aggregates of beads and microspheres together. Few instances of nonspecific aggregation were observed.

As an additional test that neutravidin was operably bound to the fluorescent microspheres, a dot blot was performed in a microfuge tube. Approximately $1.4 \times 10^6$ fluorescent microspheres were placed in a 1.5 ml microfuge tube. Added to the tube was a blocking solution (1% dry non-fat milk, 0.05% detergent, in buffer) for an incubation of 1 hour. The fluorescent microspheres were then pelleted by centrifugation. The fluorescent microspheres were then resuspended in 1 μg/ml biotin-labeled rabbit anti-mouse IgG in blocking solution, incubated for one hour, and then followed by several cycles of pelleting and washing. The fluorescent microspheres were then resuspended in 1 μg/ml horseradish peroxidase-labeled goat anti-rabbit-IgG in blocking solution, incubated for one hour, and then followed by several cycles of pelleting and washing. The fluorescent microspheres were then resuspended in a color development reagent (DAB) for 15 minutes, and then washed to remove excess color development solution. By visual examination, the fluorescent microspheres were strongly stained dark brown, indicating that neutravidin was operably bound to the surface of the fluorescent microspheres.

These illustrative examples show that affinity ligand may be operably bound to fluorescent microspheres while retaining the ability of the bound affinity ligand to interact with a analyte for which it has binding specificity.

EXAMPLE 4

This example illustrates another embodiment of fluorescent microspheres according to the present invention, and further illustrates a method of making the fluorescent microspheres according to the present invention. In this illustrative embodiment the fluorescent microspheres comprised fluorescent nanocrystals operably bound to polymeric microspheres comprising a magnetic responsive material ("magnetic material") with a polymeric, nonmagnetic coating. Such polymeric microspheres are known to include general characteristics as follows. First, magnetic materials useful for the microspheres may include, but are not limited to, ferromagnetic, ferrimagnetic, paramagnetic, superparamagnetic materials, and the like. Such magnetic materials may include, but are not limited to: metals, such as nickel, iron, cobalt, chromium, manganese, and the like; lanthanide series elements, such as neodymium, erbium, and the like; alloys such as magnetic alloys of metals; metal oxides, such as ferric oxide, chromium oxide, nickel oxide, and the like; composites, such as ferrites, magnetite, and the like; and combinations thereof. As will be appreciated by those skilled in the art, the diameter of a core of magnetic material core may vary widely depending on the size of the polymeric microsphere of which it is a part; the composition, shape, size and density of the magnetic material; and the assay protocol in which the polymeric microsphere is used. In a preferred embodiment, the diameter of a magnetic material core is a size in the range of from about 0.01 μm to about 10 μm. Polymeric materials into which may be embedded the magnetic material, or with which may be used to coat a magnetic material core, have been previously described herein in more detail. As known to those skilled in the art, the polymeric microspheres comprising magnetic material may comprise: a magnetic material core and a polymeric, nonmagnetic coating; a nonmagnetic core (e.g., polymeric or other nonmagnetic material) with a magnetic material layer thereon, and a polymeric, nonmagnetic coating; a magnetic material embedded within a polymeric, nonmagnetic material; and a magnetic material dispersed within a polymeric, nonmagnetic material (such as may be obtained by mixing the magnetic material into a solution of a thermoplastic, and then plasticizing the mixture into a solid composite).

In this illustrative example, the commercially-obtained polymeric microspheres comprised polymer-coated magnetite which were also coated with affinity ligand (either streptavidin (2.8 $\mu$m diameter), or goat anti-mouse IgG (4.5 $\mu$m diameter) on the surface of the microspheres. Thus, this example is also illustrative of an embodiment according to the present invention wherein polymeric microspheres comprising affinity ligand operably bound thereto, are then contacted with fluorescent nanocrystals under suitable conditions for the fluorescent nanocrystals to become operably bound thereto. Approximately $6.7 \times 10^7$ polymeric microspheres (in a volume of 100 $\mu$l aqueous solution) was mixed with 100 $\mu$l of a 10 $\mu$M fluorescent nanocrystal solution, and the mixture was gently agitated at room temperature for 60 minutes. The resultant fluorescent microspheres formed were then collected by centrifugation (e.g., 2 minutes at 2000×g), washed with an aqueous solution, and then collected by centrifugation again. To confirm the formation of fluorescent microspheres, the resultant microspheres were suspended in a non-aqueous medium, and placed onto a slide for viewing by fluorescence microscopy. The results in Table 4 are illustrative of the fluorescence emitted by fluorescent microspheres according to the present invention. Fluorescent microspheres comprise fluorescent nanocrystals (e.g., homocysteine-coated (CdSe) ZnS) operably bound to the magnetic polymeric microspheres having streptavidin operably bound thereto ("type A"); fluorescent microspheres comprise fluorescent nanocrystals (e.g., homocysteine-coated (CdSe)ZnS; different in size than type A) operably bound to magnetic polymeric microspheres having streptavidin operably bound thereto ("type B"); fluorescent microspheres comprise fluorescent nanocrystals (e.g., mercaptocarboxylic acid-coated (CdSe)ZnS) operably bound to magnetic polymeric microspheres having streptavidin operably bound thereto ("type C"); fluorescent microspheres comprise fluorescent nanocrystals (e.g., (CdSe)ZnS nanocrystals comprising a first coat comprising mercaptocarboxylic acid, and a second coat comprising diaminocarboxylic acid) operably bound to magnetic polymeric microspheres having streptavidin operably bound thereto ("type D"); a control "A" comprising only polymeric microspheres having streptavidin operably bound thereto; fluorescent microspheres comprise fluorescent nanocrystals (e.g., mercaptocarboxylic acid-coated (CdSe)ZnS) operably bound to magnetic polymeric microspheres having antibody (IgG) operably bound thereto ("type E"); fluorescent microspheres comprise fluorescent nanocrystals (e.g., (CdSe)ZnS nanocrystals comprising a first coat comprising mercaptocarboxylic acid, and a second coat comprising diaminocarboxylic acid) operably bound to magnetic polymeric microspheres having antibody operably bound thereto ("type F"); and a control "B" comprising only polymeric microspheres having antibody operably bound thereto. In the fluorescence analysis, the excitation spectrum was from about 360 to about 380 nm. The resultant respective emission, as described by the color observed using the fluorescence microscope is listed for each type of microsphere.

TABLE 4

| Microsphere type | Fluorescence emission |
| --- | --- |
| type A | orangish red |
| type B | yellowish green |
| type C | orange |
| type D | yellow |
| type E | orangish red |
| type F | yellow |
| control A | dim yellow (weak autofluorescence) |
| control B | — |

The following example illustrates (a) a test that affinity ligand of the polymeric microspheres was still functional (e.g., could bind to analyte for which it has binding specificity) after fluorescent nanocrystals were operably bound to the polymeric microspheres in forming fluorescent microspheres according to the present invention; and (b) a method of using the fluorescent microspheres to detect an analyte in a sample. Approximately $1.4 \times 10^6$ fluorescent microspheres (as produced according to this Example; and comprising streptavidin as affinity ligand) in 10 $\mu$l of aqueous solution was mixed and incubated with approximately $6 \times 10^5$ biotinylated polystyrene beads (6.7 $\mu$m in diameter) for 30 minutes at room temperature. The mixture comprising fluorescent microspheres and polystyrene beads was washed with aqueous solution and vigorously mixed to break up any clumping do to non-specific aggregation. The microspheres and beads were centrifuged, resuspended in DMSO, mixed again, and then mounted on a microscope slide with a coverslip. The slide was then examined under bright-field and fluorescence microscopy. The analysis showed that nearly all biotinylated polystyrene beads were bound to fluorescent microspheres. The observed binding included large aggregates of beads and microspheres together. Few instances of non-specific aggregation were observed. This illustrative example shows that fluorescent nanocrystals may be operably bound to polymeric microspheres comprising affinity ligand in forming fluorescent microspheres which retain the ability of the affinity ligand to interact with a analyte for which it has binding specificity.

EXAMPLE 5

This example illustrates one embodiment of a method of using the fluorescent microspheres according to the present invention to provide an identifiable fluorescence signal pattern. For example, semiconductor nanocrystals can be produced in several uniform sizes, with each size comprising a homogeneous population capable of emitting a discrete fluorescence emission of high quantum yield (i.e., the particular color emitted is primarily dependent on the size of the nanocrystal), but wherein the heterogeneous population (a combination of homogeneous populations) can be excited with a single wavelength spectrum of light, and can emit a distinguishably detectable ("discrete") fluorescence emission spectra representative of the homogenous populations. Likewise, depending on the dopant for a doped metal oxide nanocrystal, a homogeneous population (e.g., containing the same type and amount of dopant) is capable of emitting a discrete fluorescence emission of high quantum yield, but wherein the heterogeneous population (a combination of homogeneous populations) can be excited with a single wavelength spectrum of light, and can emit a distinguishably detectable fluorescence emission spectra representative of the homogenous populations. Thus, a fluorescent microsphere may comprise an identifiable fluorescence signal pattern comprised of one (e.g., capable of fluorescing a single color) or more (capable of fluorescing in multicolor) homogeneous populations of fluorescent nanocrystals which comprise a part (component) of the fluorescent microsphere. For example, where the fluorescent microsphere comprises a homogeneous population of fluorescent nanocrystals, the fluorescent naocrystals may be dispersed over the general shape of the fluorescent microsphere, or may be spatially arranged (e.g., multiple deposits ("localizations") on the polymeric microsphere which may be controlled by controlling the availability and location of reactive functionalities on the polymeric microsphere to which the fluorescent nanocrystals become operably bound) in providing a fluorescence signal pattern comprised of a single color of fluorescence, and as measured by a peak intensity. Likewise, where the fluorescent microsphere comprises a heterogeneous population of fluorescent nanocrystals, the fluorescent nanocrystals may be dispersed over the general shape of the fluorescent microsphere, or may be spatially arranged (e.g., multiple deposits ("localizations") on the polymeric microsphere which may be controlled by controlling the availability and location of reactive functionalities on the polymeric microsphere to which the fluorescent nanocrystals become operably bound) in providing a fluorescence signal pattern comprised of more than one color of (multicolor) fluorescence with each color capable of being detectably distinguishable from the other colors. Also, a fluorescence signal pattern emitted by a fluorescent microsphere may comprise a multicolor fluorescence, and may comprise detectably distinguishable intensities of one or colors. A code representative of the fluorescence signal pattern, and of the fluorescent microsphere which emits the fluorescence signal pattern, may comprise an identifier (e.g., one or more numbers) for each color comprising the fluorescence signal pattern, and may further comprise an identifier representative of the intensity of each color comprising the fluorescence signal pattern (e.g., wherein the code comprises a combination of the identifiers, such as a string of numbers in a range of from about 2 numbers to about 100 numbers). Thus, an identifiable fluorescence signal pattern comprised of a plurality of colors (or colors and intensities) enables a large number of combinations and permutations which may be used to identify or track a fluorescent microsphere by exposing the fluorescent microsphere to an exciting light source and detecting the resultant fluorescence emission. Thus, fluorescent microspheres may be used in multidimensional array formats (e.g., microarrays) for detecting a plurality of analytes by depositing on and/or flowing the fluorescent microspheres in the desired array format, and utilizing an appropriate detection system to detectably distinguish the fluorescent signal patterns (e.g., as measured by number of events of fluorescence versus the intensity of fluorescence, using a fluorescence microscope with a video camera attachment and computer software program for manipulating and storing the data collected).

EXAMPLE 6

This example illustrates another embodiment of a method of using the fluorescent microspheres according to the present invention for determining the presence or absence of a predetermined number of analytes in a sample. The determination may be qualitative or quantitative, depending on the assay format utilized. A predetermined number of analytes means a single analyte if it is desired to determine the presence or absence of that analyte alone; or more than one analyte when it is desired to determine the presence or absence of any one of multiple analytes. The fluorescent microspheres may comprise a homogenous population which is capable of fluorescing a peak emission (fluorescent signal pattern) when excited by an excitation light source, and further comprises affinity ligand having binding specificity for the analyte of which the presence or absence is to be determined. Alternatively, the fluorescent Imicrospheres may comprise a heterogeneous population comprising multiple homogenous populations, wherein each homogenous population is capable of emitting a fluorescence signal pattern distinguishable from the fluorescence signal patterns of other homogenous populations comprising the heterogeneous population, and wherein the heterogeneous population may be excited by a single excitation light source. Each homogenous population may further comprise affinity ligand having binding specificity for an analyte of the predetermined number of analytes of which the presence or absence is to be determined. Thus, a method of using the fluorescent microspheres for determining the presence or absence of a predetermined number of analytes in a sample comprises:

(a) contacting the fluorescent microspheres with the sample under suitable conditions for the fluorescent microspheres to bind the predetermined number of analytes, if present in the sample, in forming complexes;

(b) exposing the complexes, if formed, to an excitation wavelength light source suitable for exciting the fluorescent microspheres of the complexes to emit a fluorescence signal pattern; and (c) detecting the fluorescence signal pattern emitted by the complexes, if present, by a detection means for detecting the fluorescence signal pattern;

wherein detection of the fluorescent signal pattern is indicative of the presence of an analyte of the predetermined number of analytes. Wherein the presence of an analyte is detected, the method may further comprise quantitating the amount of analyte by measuring the intensity of the fluorescence signal pattern emitted from the fluorescent microspheres bound to the analyte, and relating the intensity measured to the amount of analyte. The method may be used in a fluorescent detection system selected from the group consisting of an affinity-based assay, fluorescencebased immunoassay, fluorescent staining (e.g., immunofluorescent staining on a glass slide), flow cytometry, a hybridization-based assay, and the like.

In a preferred embodiment, the fluorescence signal pattern comprises one or more fluorescence emission peaks, wherein each peak has a narrow spectral band (e.g. between about 4 nm to about 50 nm) in the range of from about 400 nm to about 800 nm. A preferred excitation light source for exciting the fluorescent microspheres according to the present invention is in the range of about 300 nm to about 400 nm; and in a more preferred embodiment, from about 360 nm to about 365 nm. Any fluorescence signal pattern emitted is then detected and imaged by appropriate detection means or system (e.g., one or more of: photodetector, filter, charge couple device camera (CCD camera) fluorimeter, fluorescence microscope, a fluorescence cube, a computer for manipulating fluorescence signal pattern data collected, and a combination thereof)

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed:

1. A fluorescent microsphere comprised of a plurality of fluorescent nanocrystals operably bound to a polymeric microsphere, wherein the fluorescent nanocrystals are functionalized with a plurality of molecules selected from the group consisting of carboxylic acid, diaminocarboxylic acid, monoaminocarboxylic acid, and a combination thereof.

2. The fluorescent microsphere according to claim 1, wherein the polymeric microsphere comprises multiple molecules of reactive functionality comprising a free chemical group, and the fluorescent nanocrystals comprise multiple molecules of reactive functionality comprising a reactive chemical group which are operably bound to the reactive functionality of the polymeric microsphere.

3. The fluorescent microsphere according to claim 1, wherein operably bound to the polymeric microsphere is a homogeneous population of fluorescent nanocrystals.

4. The fluorescent microsphere according to claim 1, wherein operably bound to the polymeric microsphere is a heterogeneous population of fluorescent nanocrystals.

5. The fluorescent microsphere according to claim 1, further comprising affinity ligand operably bound thereto.

6. The fluorescent microsphere according to claim 1, wherein the fluorescent nanocrystals have an average particle size of approximately 1 nm to approximately 20 nm.

7. The fluorescent microsphere according to claim 1, wherein the fluorescent nanocrystals comprise semiconductor nanocrystals.

8. The fluorescent microsphere according to claim 7, wherein the fluorescent nanocrystals have a particle size that varies by less than 4%.

9. The fluorescent microsphere according to claim 1, wherein the fluorescent nanocrystals comprise doped metal oxide nanocrystals.

10. The fluorescent microsphere according to claim 9, wherein the fluorescent microsphere is magnetic.

11. The fluorescent microsphere according to claim 1, wherein the polymeric microsphere comprises a material selected from the group consisting of latex, acrylic, a glass/polymer composite, a thermoplastic, a polymeric material in combination with a magnetic material, and a combination thereof.

12. The fluorescent microsphere according to claim 11, wherein the polymeric microsphere further comprises carbon black in a weight percentage of from about 0.5 to about 5.

13. The fluorescent microsphere according to claim 1, wherein the polymeric microsphere comprises a combination of a polymeric material and a magnetic material selected from the group consisting of a polymeric material into which is embedded the magnetic material, a magnetic material core and a polymeric material coating, a polymeric material core with a magnetic material layer thereon and a polymeric material coating over the magnetic layer, and a magnetic material dispersed within a polymeric material.

14. The fluorescent microsphere according to claim 3, wherein the homogenous population of fluorescent nanocrystals, when excited with an excitation light source, emit a fluorescence signal pattern.

15. The fluorescent microsphere according to claim 4, wherein the heterogeneous population of fluorescent nanocrystals, when excited with an excitation light source, emit a fluorescence signal pattern.

16. The fluorescent microsphere according to claim 15, wherein the fluorescence signal pattern comprises multicolor fluorescence and detectably distinguishable intensities.

17. The fluorescent microsphere according to claim 16, wherein a code representative of the fluorescence signal pattern, and of the fluorescent microsphere which emits the fluorescence signal pattern, comprises an identifier for each color comprising the fluorescence signal pattern, and an identifier for the intensity of each color.

18. The fluorescent microsphere according to claim 17, wherein the code comprises a string of numbers.

19. A code representative of the fluorescence microsphere according to claim 17.

20. A code representative of the fluorescence microsphere according to claim 18.

21. A method of producing a fluorescent microsphere comprised of a plurality of fluorescent nanocrystals operably bound to a polymeric microsphere, wherein the method comprises contacting the polymeric microsphere with a plurality of fluorescent nanocrystals under suitable conditions for the plurality of fluorescent nanocrystals to become operably bound to the polymeric microsphere.

22. The method according to claim 21, wherein the polymeric microsphere comprises multiple molecules of reactive functionality comprising a free chemical group, and the fluorescent nanocrystals comprise multiple molecules of reactive functionality comprising a reactive chemical group which become operably bound to the reactive functionality of the polymeric microsphere.

23. The method according to claim 21, wherein operably bound to the polymeric microsphere is a homogenous population of fluorescent nanocrystals.

24. The method according to claim 21, wherein operably bound to the polymeric microsphere is a heterogeneous population of fluorescent nanocrystals.

25. The method according to claim 21, wherein the fluorescent microsphere further comprises affinity ligand operably bound thereto.

26. The method according to claim 21, wherein the fluorescent nanocrystals have an average particle size of approximately 1 nm to approximately 20 nm.

27. The method according to claim 21, wherein the fluorescent nanocrystals comprise semiconductor nanocrystals.

28. The method according to claim 21, wherein the fluorescent nanocrystals have a particle size that varies by less than 4%.

29. The method according to claim 21, wherein the fluorescent nanocrystals comprise doped metal oxide nanocrystals.

30. The method according to claim 29, wherein the fluorescent microsphere is magnetic.

31. The method according to claim 21, wherein the polymeric microsphere comprises a material selected from the group consisting of latex, acrylic, a glass/polymer composite, a thermoplastic, a polymeric material in combination with a magnetic material, and a combination thereof.

32. The method according to claim 21, wherein the polymeric microsphere further comprises carbon black in a weight percentage of from about 0.5 to about 5.

33. The method according to claim 21, wherein the polymeric microsphere comprises a combination of a polymeric material and a magnetic material selected from the group consisting of a polymeric material into which is embedded the magnetic material, a magnetic material core and a polymeric material coating, a polymeric material core with a magnetic material layer thereon and a polymeric material coating over the magnetic layer, and a magnetic material dispersed within a polymeric material.

34. A method of using fluorescent microspheres for determining the presence or absence of a predetermined number of analytes in a sample, wherein a fluorescent microsphere comprises a plurality of fluorescent nanocrystals operably bound to a polymeric microsphere and further comprises affinity ligand operably bound thereto, the method comprising:

(a) contacting the fluorescent microspheres with the sample under suitable conditions for the fluorescent microspheres to bind the predetermined number of analytes, if present in the sample, in forming complexes;

(b) exposing the complexes, if formed, to an excitation wavelength light source suitable for exciting the fluorescent microspheres of the complexes to emit a fluorescence signal pattern; and (c) detecting the fluorescence signal pattern emitted by the complexes, if present, by a detection means for detecting the fluorescence signal pattern;

wherein detection of the fluorescent signal pattern is indicative of the presence of an analyte of the predetermined number of analytes.

35. The method according to claim 34, wherein the presence of an analyte is detected, and the method further comprises quantitating an amount of the analyte detected by measuring the intensity of the fluorescence signal pattern emitted from the fluorescent microspheres bound to the analyte.

36. The method according to claim 34, wherein the method is performed using a fluorescent detection system selected from the group consisting of an affinity-based assay, fluorescence-based immunoassay, fluorescent staining, flow cytometry, and a hybridization-based assay.

37. The method according to claim 34, wherein the fluorescence signal pattern comprises one or more fluorescence emission peaks, wherein each peak has a narrow spectral band in the range of from about 400 nm to about 800 nm.

38. The method according to claim 34, wherein the excitation wavelength light source for exciting the fluorescent microspheres is a wavelength spectrum in the range of about 300 nm to about 400 nm.

39. The method according to claim 34, wherein the detection means is selected from the group consisting of a photodetector, a filter, a charge couple device camera, a fluorimeter, a fluorescence microscope, a fluorescence cube, a computer for manipulating fluorescence signal pattern data collected, and a combination thereof.

* * * * *